US009675617B2

(12) United States Patent
Gustavsson et al.

(10) Patent No.: US 9,675,617 B2
(45) Date of Patent: Jun. 13, 2017

(54) TETRAHYDROFOLATES IN COMBINATION WITH EGFR-INHIBITORS

(71) Applicant: ISOFOL MEDICAL AB, Göteborg (SE)

(72) Inventors: Bengt Gustavsson, Västra Frölunda (SE); Björn Carlsson, Västra Frölunda (SE)

(73) Assignee: ISOFOL MEDICAL AB, Gothenburg (SE)

( * ) Notice: Subject to any disclaimer, the term of this patent is extended or adjusted under 35 U.S.C. 154(b) by 185 days.

(21) Appl. No.: 14/372,701

(22) PCT Filed: Jan. 18, 2013

(86) PCT No.: PCT/EP2013/050973
§ 371 (c)(1),
(2) Date: Jul. 16, 2014

(87) PCT Pub. No.: WO2013/107883
PCT Pub. Date: Jul. 25, 2013

(65) Prior Publication Data
US 2015/0017158 A1    Jan. 15, 2015

(30) Foreign Application Priority Data

Jan. 20, 2012  (EP) .................................... 12151993

(51) Int. Cl.
| | |
|---|---|
| A61K 31/519 | (2006.01) |
| A61K 39/395 | (2006.01) |
| C07K 16/28 | (2006.01) |
| A61K 45/06 | (2006.01) |
| A61K 31/44 | (2006.01) |
| A61K 31/4704 | (2006.01) |
| A61K 39/00 | (2006.01) |

(52) U.S. Cl.
CPC ............ *A61K 31/519* (2013.01); *A61K 31/44* (2013.01); *A61K 31/4704* (2013.01); *A61K 39/3955* (2013.01); *A61K 39/39558* (2013.01); *A61K 45/06* (2013.01); *C07K 16/2863* (2013.01); *A61K 2039/505* (2013.01)

(58) Field of Classification Search
None
See application file for complete search history.

(56) References Cited

U.S. PATENT DOCUMENTS

| 5,376,658 A | 12/1994 | Spears et al. |
| 2007/0099866 A1 | 5/2007 | Moser et al. |
| 2007/0280944 A1 | 12/2007 | Robbins et al. |
| 2011/0052581 A1 | 3/2011 | Karlin et al. |

FOREIGN PATENT DOCUMENTS

| JP | 2007-515482 A | 6/2007 |
| JP | 2007-531728 A | 11/2007 |
| JP | 2009-518305 A | 5/2009 |
| WO | WO 2004/112761 A2 | 12/2004 |
| WO | WO 2005/060973 A1 | 7/2005 |
| WO | WO-2005/060973 A1 | 7/2005 |
| WO | WO2005/097086 | * 10/2005 |
| WO | WO 2007/064968 A2 | 6/2007 |
| WO | WO-2007/064968 A2 | 6/2007 |
| WO | WO 2008/109349 A1 | 9/2008 |
| WO | WO-2010/022201 A2 | 2/2010 |

OTHER PUBLICATIONS

Van Cutsem et al (Journal of Clinical Oncology, 2011, vol. 29, pp. 2011-2019).*
Messersmith et al (Clinical Cancer Research, vol. 10, pp. 6522-6527).*
Douillard et al (Journal of Clinical Oncology, 2010, vol. 28, pp. 4697-4705).*
Fukai et al, Cancer Science, 2008, vol. 99, pp. 2062-2069.*
Cunningham et al., "Cetuximab Monotherapy and Cetuximab plus Irinotecan in Irinotecan-Refractory Metastatic Colorectal Cancer", N. Engl. J. Med. (2004), vol. 351, pp. 337-345.
Jonker et al, "Cetuximab for the Treatment of Colorectal Cancer", N. Engl. J. Med. (2007), vol. 357, pp. 2040-2048.
Garrett and Eng, "Cetuximab in the Treatment of patients with colorectal cancer", Expert Opin. Biol. Ther. (2011), vol. 11, pp. 937-949.
Lenz, "Cetuximab in the management of colorectal cancer", Biologics (2007), vol. 1, pp. 77-91.
Ulrich and Potter, "Folate Supplementation: Too Much of a Good Thing?", Cancer Epidemiol Biomarkers Prev (2006), vol. 15, pp. 189-193.
Kim, "Folate: a magic bullet or a double edged sword for colorectal cancer prevention?", Gut (2006), vol. 55, pp. 1387-1389.
Ulrich, "Folate and cancer prevention: a closer look at a complex picture", Am. J. Clin. Nutr. (2007), vol. 86, pp. 271-273.
Borsi et al, "Rescue After Intermediate and High-Dose Methotrexate: Background, Rationale, and Current Practice", Pediatric Hematology and Oncology 1990, vol. 7, pp. 347-363.
Sirotnak FM, and Tolner B, "Carrier-mediated membrane transport of folates in mammalian cells"; Annu Rev Nutr 1999;19:91-122.
Shane B, "Folylpolyglutamate synthesis and role in the regulation of one-carbon metabolism"; Vitam Horm 1989;45:263-335.
Spears C. P. et al, "Deoxyuridylate effects on thymidylate synthase-5-fluorodeoxyuridylate-folate ternary complex formation"; Biochem Pharmacol 1989; 38:2985-2993.

(Continued)

*Primary Examiner* — Karen Canella
(74) *Attorney, Agent, or Firm* — Harness, Dickey and Pierce, P.L.C.

(57) ABSTRACT

The present invention relates a pharmaceutical composition comprising an EGFR inhibitor and methylene-tetrahydrofolate, tetrahydrofolate or methyl-tetrahydrofolate, for use in the treatment of cancer. The methylene-tetrahydrofolate, tetrahydrofolate or methyl-tetrahydrofolate enhances the anticancer efficacy of the EGFR inhibitor. The cancers that may be treated include breast cancer, gastric cancer, gastrointestinal cancer, gall bladder cancer, bile duct cancer, colon cancer, rectal cancer, liver cancer, pancreatic cancer, head and neck cancer, esophageal cancer, mesothelioma cancer, lung cancer including non-small-cell lung cancer, ovarian cancer, endometrial cancer, cervical cancer, peripheral T-cell lymphoma (PTCL), melanoma, brain tumors, adenocarcinoma, esophageal cancer, and osteosarcoma.

19 Claims, 4 Drawing Sheets

(56) References Cited

OTHER PUBLICATIONS

Spears C. P., et al "Thymidylate synthetase inhibition in malignant tumors and normal liver of patients given intravenous 5-fluorouracil", Cancer Res 1984; 44:4144-4150.

Galivan J. et al, "Glutamyl hydrolase: Pharmacological role and enzymatic characterization", Pharmacol Ther 2000;85:207-215.

Chéradame, S. et al., "Relevance of tumoral folypolyglutamate synthetase and reduced folates for optimal 5-fluorouracil efficacy: Experimental data", European Journal of Cancer, Pergamon Press, Oxford, GB, vol. 33, No. 6, May 1, 1997 (May 1, 1997), pp. 950-959, XP027383482, ISSN: 0959-8049, [retrieved on May 1, 1997], p. 951, left-hand column, last paragraph.

International Search Report and Written Opinion of the ISA, ISA/EP, mailed Mar. 6, 2013.

Office Action Dated Nov. 1, 2016 Issued in Corresponding Japanese Patent Application No. JP 2014-552645.

Office Action Dated Sep. 12, 2016 Issued in Corresponding Russian Patent Application No. 2014134050/15(055034).

Office Action dated Nov. 15, 2016 Issued in Corresponding Chinese Patent Application (Chinese Only).

Zanni, G. (2007) "Colorectal Cancer: A New Paradigm" Pharmacy Times.

First Examination Report dated Apr. 30, 2015 for New Zealand Patent Document No. IP 626271.

\* cited by examiner

TETRAHYDROFOLATES IN COMBINATION WITH EGFR-INHIBITORS

CROSS REFERENCE TO RELATED APPLICATIONS

This application is a 371 National Phase of PCT/EP2013/050973, filed on Jan. 18, 2013, which claims the benefit and priority of European Patent Application EP 12151993.8, filed on 20 Jan. 2012. The entire disclosures of each of the above applications are incorporated herein by reference.

FIELD

The present disclosure relates to use of EGFR inhibitors and reduced folates for the treatment of cancer.

BACKGROUND

Cancer is one of the world's largest health concerns. It is one of the major leading causes of deaths worldwide and together with cardiovascular diseases, diabetes, chronic respiratory diseases it causes over 60% of all deaths globally. Nearly 12.7 million new cancer cases and 7.6 million cancer deaths occurred in 2008 worldwide.

Colorectal cancer (CRC) is the third most common cancer in men and the second in women worldwide. Almost 60% of the cases occur in developed regions. Incidence rates vary worldwide, but are overall substantially higher in men than in women. Over 600 000 people die each year from the disease, accounting for 8% of all cancer-related deaths. In the US alone, over 150 000 new cases are diagnosed each year. Colon cancer is defined as cancer that forms in the tissues of the colon (the longest part of the large intestine). Most colon cancers are adenocarcinomas (cancers that begin in cells that make and release mucus and other fluids).

Cancer of the colon is a highly treatable and often curable disease when localized to the bowel. Surgery is the primary form of treatment and results in cure in approximately 50% of the patients. Recurrence following surgery is a major problem and is often the ultimate cause of death. Nearly half of the colorectal cancer cases are metastatic or develop into a metastasized disease. In these cases, chemotherapy is the sole treatment option and the prognosis for the patient is often rather poor. Similarly, treatment regimens for other forms of cancer do not lead to full recovery of all patients and many cancers recur and/or develop into metastatic forms.

There is therefore a great need for new and improved drug-based therapies to combat not only colorectal cancer, but also a number of other cancer indications such as, for example, breast cancer, gastric cancer, gastrointestinal cancer, gall bladder cancer, bile duct cancer, colon cancer, rectal cancer, liver cancer, pancreatic cancer, head and neck cancer, esophageal cancer, mesothelioma cancer, lung cancer including non-small-cell lung cancer, ovarian cancer, endometrial cancer, cervical cancer, peripheral T-cell lymphoma (PTCL), melanoma, brain tumors, adenocarcinoma, esophageal cancer, and osteosarcoma.

The epidermal growth factor receptor (EGFR) is a tyrosine kinase that, when stimulated, activates several signaling pathways, including the MAPK, Akt and JNK pathways. Activation of the proteins involved in these pathways ultimately leads to DNA synthesis and cell proliferation, and the EGFR pathway has been shown to be activated in a wide variety of cancers, including CRC. Thus, EGFR is an attractive target for anti-cancer therapy. Several EGFR inhibitors have therefore been developed for use in cancer treatment. These include monoclonal antibodies such as cetuximab and panitumumab and the recently developed zalutumumab, nimotuzumab, and matuzumab, as well as small molecule drugs such as gefitinib, erlotinib, and lapatinib. Generally, the monoclonal antibodies bind to the extracellular ligand binding site of the EGFR, while the small molecules bind to and inhibit the intracellular tyrosine kinase part of the EGFR.

Cetuximab (Erbitux®) and panitumumab (Vectibix®) are monoclonal antibodies and EGFR inhibitors. They exert their inhibition by binding to the extracellular domain of EGFR, thus preventing binding of the natural ligand and activation of the receptor. Cetuximab is a chimeric mouse/human monoclonal antibody of the IgG1 isotype, while panitumumab is a fully human antibody of the IgG2 isotype.

Cetuximab is currently used for second and third line treatment of metastatic colorectal cancer (mCRC), in cases where the tumor expresses EGFR and wild-type KRAS (Kirsten ras sarcoma viral oncogene). KRAS is a guanosine triphosphate-(GTP-) binding protein downstream of the EGFR and is a central component of the mitogen-activated protein kinase (MAPK) pathway, which is a component of the EGFR signaling cascade. KRAS mutations lead to EGFR-independent constitutive activation of the signaling pathway and is associated with a lack of response and benefit from EGFR inhibitors such as cetuximab and panitumumab. Roughly 40% of colorectal cancers are characterized by a mutation in the KRAS gene. About 90% of these mutations occur in codons 12 and 13 in exon 2 of the KRAS gene, with the remaining mutations occurring in codons 61 and 146 (roughly 5% each).

Cetuximab has been shown useful to overcome acquired resistance to irinotecan chemotherapy and is thus used in combination with irinotecan in patients with mCRC that are refractory (resistant) to irinotecan. It is also used as a single agent in patients with mCRC after irinotecan and oxaliplatin-based regimens that have failed or in patients that are intolerant to irinotecan-based regimens.

Furthermore, cetuximab is used for treatment of patients with various stages of squamous cell carcinoma of the head and neck, either in combination with radiation therapy or together with or after platinum-based therapy.

Panitumumab is used for treatment of refractory EGFR-expressing metastatic colorectal cancer in patients with non-mutated KRAS, i.e. where other prior treatment has failed.

Although EGFR inhibitors initially held great promise as anti-cancer agents, and indeed still have valuable uses, they are also associated with some drawbacks. When used in a treatment naïve setting (i.e. in patients without prior treatment) as a single agent, the efficacy of cetuximab has been poor, not yielding any substantial improvement in survival of the patients. Also, when used in different combination treatments with e.g. FOLFIRI (5-fluorouracil (5-FU), leucovorin and irinotecan), FOLFOX (5-FU, leucovorin and oxaliplatin) or CAPOX (capecitabine and oxaliplatin), cetuximab improved survival times when combined with FOLFIRI, but yielded uncertain improvement in response rates or survival times for the other combinations (for review see Garrett and Eng, Expert Opin. Biol. Ther. (2011), vol. 11, pages 937-949).

The benefits of cetuximab treatment are more evident in a chemotherapy-refractory setting, i.e. where other treatments have failed, where cetuximab has been shown to improve response rates both when used as a single agent and in combination with irinotecan (Cunningham et al, N. Engl.

J. Med. (2004), vol. 351, pages 337-345; Jonker et al, N. Engl. J. Med. (2007), vol. 357, pages 2040-2048). Improvement in survival in this setting was shown to be rather modest, i.e. a few months.

Cetuximab treatment is associated with some serious and some adverse side reactions, including severe allergic infusion reactions, cardiopulmonary arrest, dermatologic toxicity and hypomagnesemia (Garreth and Eng, Expert Opin. Biol. Ther. (2011), vol. 11, pages 937-949; Lenz, Biologics (2007), vol. 1, pages 77-91). The most frequently observed toxicity from cetuximab is rash; the majority of patients develop an acne-form rash, which can have a significant psychological impact on the patient. Other common side effects include pruritus, nail changes, headache, diarrhea, infections and vomiting. Similar side reactions are observed in relation to panitumumab treatment.

Thus, there is still a need to find new treatment regimens against cancer, as well as to improve the efficacy and reduce the side effects of EGFR inhibitors such as cetuximab and panitumumab.

Folates are endogenous substances that are essential for cell division and cell growth. Intracellular reduced folates exist as a pool of at least six interconvertable forms. Folates are for instance involved in nucleotide metabolism, where they serve as substrates and/or coenzymes of various enzymes, such as thymidylate synthase (TS) and dihydrofolate reductase (DHFR). The folate methylene-tetrahydrofolate (methylene-THF), for example, acts as a one-carbon donor in the conversion between dUMP and dUTP, performed by TS. Thereby it contributes to the synthesis of thymidine and thus to the synthesis of DNA and to cell growth.

The role of folates in carcinogenesis is complex. Experimental data suggest that the timing of folate supplementation during carcinogenesis is of importance (Ulrich, Cancer Epidemiol Biomarkers Prev (2006), vol. 15, pages 189-93; Kim, Gut (2006), vol. 55, pages 1387-1389). Although increases in folate levels before the existence of preneoplastic lesions (such as aberrant crypt foci or polyps in the colon) can prevent tumor development, folate supplementation is believed to enhance cancer progression once preneoplastic lesions are present. Thus, folates are believed to inhibit cancer development when used preventively, but believed to enhance cancer progression once cancer has started to develop. Since folates are known to be involved in synthesis of nucleotides and in cell growth, it has been expected that they have such cancer promoting effect. Furthermore, cancer cells frequently up-regulate folate receptors to meet their elevated need for nucleotides to support DNA synthesis and growth, hence an increased risk of tumor growth promotion with folate administration is expected (Ulrich, Am. J. Clin. Nutr. (2007), vol. 86, pages 271-273).

Antifolates, such as methotrexate and pemetrexed, have thus been used as chemotherapeutic agents for the treatment of cancer, by being able to inhibit one or more of the enzymes involved in the folate and nucleotide metabolism, e.g. TS and/or DHFR. Fluoropyrimidines, such as 5-fluorouracil (5-FU), has similarly been used as chemotherapeutic agents, by being able to inhibit TS. Antifolates as well as fluoropyrimidines are however cytotoxic and can be associated with severe side effects for many patients.

Folic acid and folates, such as in the form of leucovorin (also known as folinic acid), levoleucuvorin and methylene-THF, have been co-administered with chemotherapeutic agents to cancer patients. Folates have for example been used as rescue agents to methotrexate, in order to reduce the toxic side effects of the methotrexate and multi targeting anti-folate treatment (Borsi et al, Pediatric Hematology and Oncology 1990, vol. 7, pages 347-363; EP 1 699 462 B1).

Folic acid, leucovorin and methylene-THF have also been used in combination with 5-FU, in order to enhance the anti-tumoral effect of 5-FU.

U.S. Pat. No. 5,376,658, US 2007/0099866 A1 and WO 2007/064968 disclose the use of tetrahydrofolate (THF) and/or methylene-THF to enhance the cytotoxic and thus chemotherapeutic effect of 5-FU.

US2007/0280944 A1 discloses the use of methylene-THF in combination with 5-FU for the treatment of cancer, based on the finding that methylene-THF not only increases the efficacy of 5-FU, but also reduces the toxicity to the patient of 5-FU. In addition, at least one additional cancer drug is administered to the patient. The one additional cancer drug may for instance be an anti-EGFR antibody such as cetuximab.

WO 2008/109349 A1 discloses a treatment regimen for treating cancer, comprising administering 5-FU and methylene-THF to the patient certain days and administering capecitabine (marketed as Xeloda®) to the patient on the days in between. Capecitabine is analogous to 5-FU, but is administered to the patient orally. In certain embodiments the treatment further includes co-administration of a chemotherapeutic agent, e.g. cetuximab.

US 2011/0052581 A1 discloses a method for treating metastatic colorectal cancer by administration of picoplatin in conjunction with cetuximab and optionally with 5-FU and leucovorin.

Thus, cetuximab has been used in conjunction with 5-FU and folates, such as leucovorin and methylene-THF. In these treatment regimens the folates have been used in order to enhance the effect of 5-FU.

SUMMARY

The present inventors have surprisingly found that folates such as methylene-THF enhance the anti-cancer effect of EGFR inhibitors such as cetuximab, even in the absence of 5-FU. That is, these folates appear to have an intrinsic ability to increase the efficacy of cetuximab treatment. The mechanism behind this property has not been elucidated but may be due either to an unexpected intrinsic anti-cancer property of the folate itself, or by a synergistic mechanism between the folate and the EGFR receptor and/or the EGFR inhibitor. The present disclosure thus demonstrates a novel combination of methylene-THF, THF or methyl-THF and an EGFR inhibitor, in absence or isolation from 5-FU, for the treatment of cancer.

The novel combination of methylene-THF, THF or methyl-THF and an EGFR inhibitor, without 5-FU, provides a cancer treatment regimen that is more efficient than using an EGFR inhibitor as a single agent, and that has less side effects as compared to a treatment regimen including 5-FU. Such a treatment regimen may for instance be useful for preventing recurrence of cancer. Furthermore, such a treatment is useful in cases where 5-FU cannot be used, e.g. because it is not tolerated by the patient.

In one aspect the disclosure provides a pharmaceutical composition comprising, as components, methylene-tetrahydrofolate, tetrahydrofolate or methyl-tetrahydrofolate and an EGFR inhibitor, for use in the treatment of cancer.

In one embodiment the pharmaceutical composition is for administration in isolation of 5-fluorouracil. In a further embodiment, the pharmaceutical composition is for administration in isolation of analogues, prodrugs and/or metabolites of 5-fluorouracil. In a still further embodiment, said 5-fluoruracil, and/or said analogues, prodrugs and/or metabolites of 5-fluoruracil are metabolized to FdUMP.

The pharmaceutical composition may be used for inhibition of tumor growth or reduction of the volume of a tumor. The tumor may be a solid or non-solid tumor, preferably a solid tumor.

In one embodiment the EGFR inhibitor is selected from gefitinib, erlotinib and lapatinib, and polyclonal or monoclonal antibody EGFR inhibitors such as cetuximab, panitumumab, zalutumumab, nimotuzumab and matuzumab, or combinations thereof. Other EGFR inhibitors that may be used for the present disclosure are listed in Table 1. In a preferred embodiment the EGFR inhibitor is a monoclonal antibody EGFR inhibitor, e.g. cetuximab and/or panitumumab.

In one embodiment the methylene-tetrahydrofolate, tetrahydrofolate or methyl-tetrahydrofolate is methylene-tetrahydrofolate, e.g. [6R]-methyl-tetrahydrofolate.

In one embodiment the methylene-tetrahydrofolate, tetrahydrofolate or methyl-tetrahydrofolate of the pharmaceutical composition is for administration no later than 24 hours before the administration of 5-FU and/or an analogue, prodrug and/or metabolite thereof. In other embodiments it is for administration no later than 36 hours or 48 hours before the administration of 5-FU and/or analogues, prodrugs and/or metabolites thereof.

In other embodiments the methylene-tetrahydrofolate, tetrahydrofolate or methyl-tetrahydrofolate of the pharmaceutical composition is for administration at the earliest 6 hours, 24 hours, 48 hours, one week or 12 days after the administration of 5-FU and/or analogues, prodrugs and/or metabolites thereof.

In still other embodiments the pharmaceutical composition is for administration no later than one week before the administration of 5-FU and/or analogues, prodrugs and/or metabolites thereof, and/or for administration at the earliest one week after the administration of 5-FU and/or analogues, prodrugs and/or metabolites thereof.

In one embodiment the pharmaceutical composition according to the present disclosure is for administration in isolation from 5-FU and/or analogues, prodrugs and/or metabolites thereof during a time period of at least three months.

The methylene-tetrahydrofolate, tetrahydrofolate or methyl-tetrahydrofolate and the EGFR inhibitor of the pharmaceutical composition may be formulated in different pharmaceutical compositions or in a common pharmaceutical composition.

In one embodiment the EGFR inhibitor is cetuximab and is administered in an amount of at least 50 mg/m$^2$, preferably at least 100 mg/m$^2$, and more preferably at least 250 mg/m$^2$, 400 mg/m$^2$ or 500 mg/m$^2$, and at maximum 1000 mg/m$^2$.

The methylene-tetrahydrofolate, tetrahydrofolate or methyl-tetrahydrofolate may be for administration in an amount of at least 10 mg/m$^2$, preferably at least 20 mg/m$^2$, more preferably at least 50 mg/m$^2$, most preferably at least 100 mg/m$^2$, 200 mg/m$^2$ or 500 mg/m$^2$, and at maximum 5 g/m$^2$.

In different embodiments the methylene-tetrahydrofolate, tetrahydrofolate or methyl-tetrahydrofolate is for administration once or twice daily, every second or third day, once to twice a week, or once every second or third week. The EGFR inhibitor may be for administration once daily, every second or third day, once to twice a week, or once every second or third week.

The pharmaceutical composition of the present disclosure may be for treatment of a cancer is selected from breast cancer, gastric cancer, gastrointestinal cancer, gall bladder cancer, bile duct cancer, colon cancer, rectal cancer, liver cancer, pancreatic cancer, head and neck cancer, esophageal cancer, mesothelioma cancer, lung cancer including non-small-cell lung cancer, ovarian cancer, endometrial cancer, cervical cancer, peripheral T-cell lymphoma (PTCL), melanoma, brain tumors, adenocarcinoma, esophageal cancer, and osteosarcoma.

In one aspect the present disclosure provides a kit containing as pharmaceutically active components a) methylene-tetrahydrofolate, tetrahydrofolate or methyl-tetrahydrofolate and b) an EGFR inhibitor. The EGFR inhibitor may be selected from gefitinib, erlotinib and antibody EGFR inhibitors such as cetuximab, panitumumab, zalutumumab, nimotuzumab and matuzumab, or EGFR inhibitors listed in Table 1.

DETAILED DESCRIPTION

Figure 2:
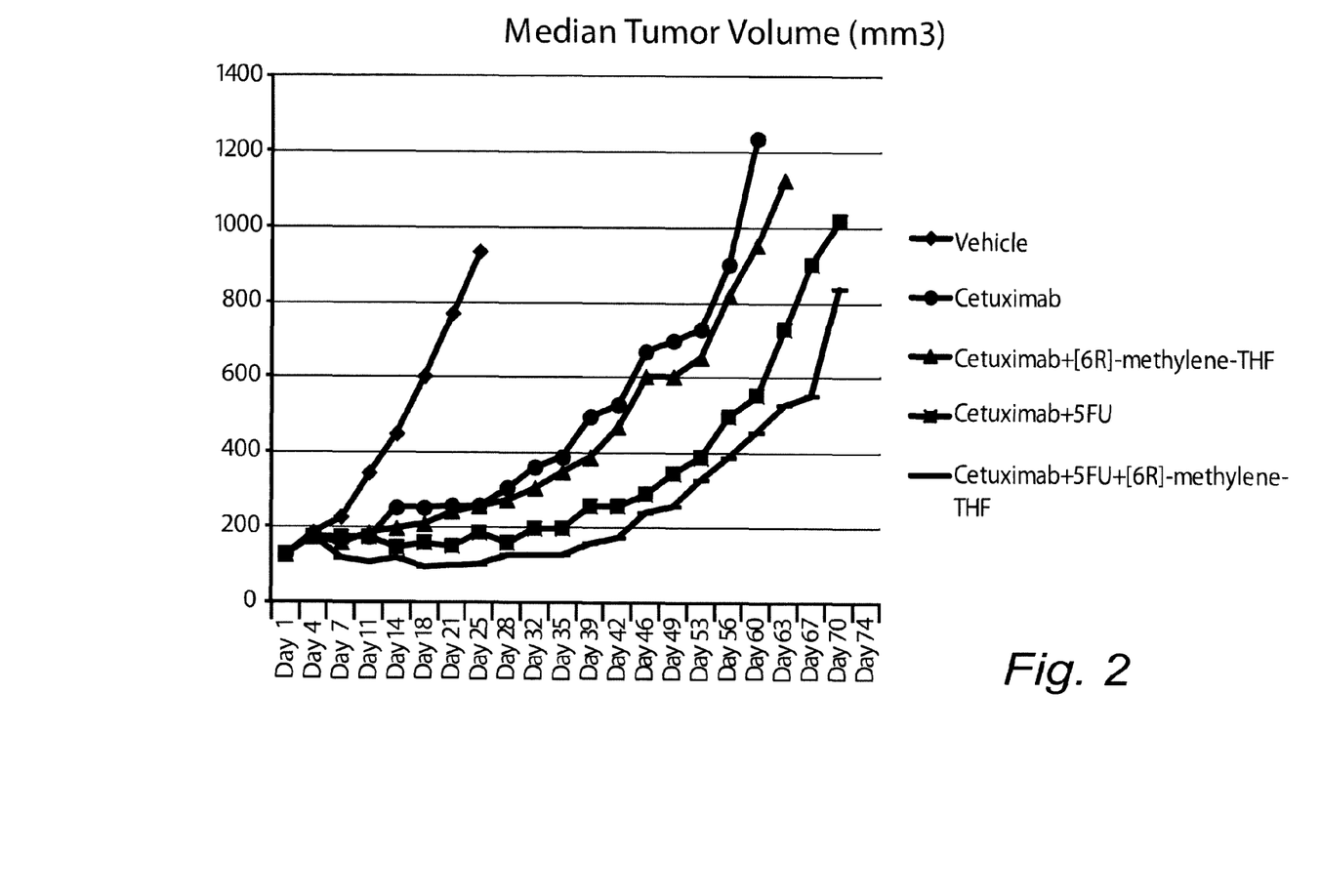
FIG. 2 shows the development of median tumor volume over time in the animal groups of example 1, receiving vehicle, cetuximab, cetuximab with methylene-THF, cetuximab with 5-FU and cetuximab with 5-FU and methylene-THF respectively.
Figure 3:
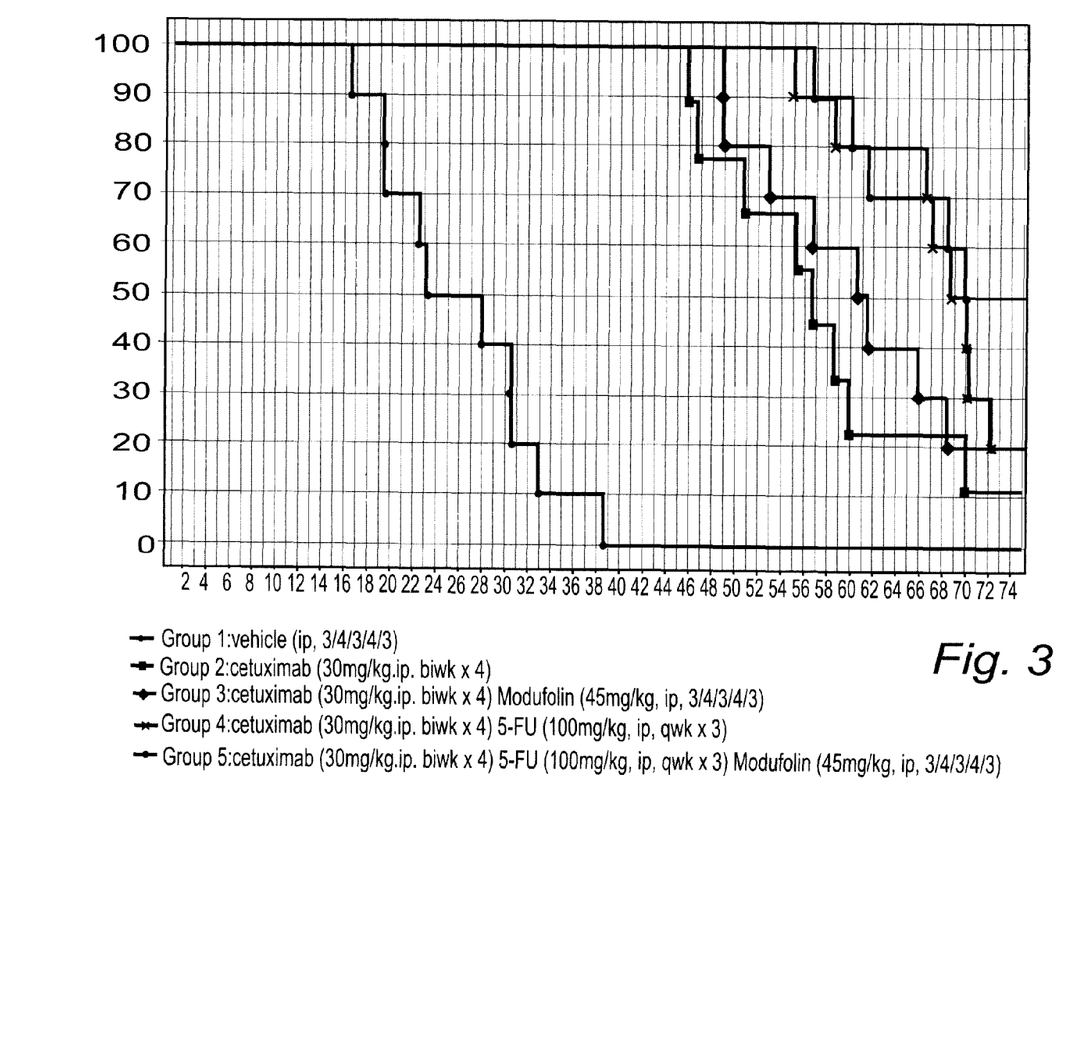
FIG. 3 shows a Kaplan Meier plot showing the time to endpoint, as defined in example 1, for the animals of the respective groups of example 1.

In the research work leading to the present disclosure, the inventors surprisingly found that methylene tetrahydrofolate (methylene-THF) has an ability to enhance the efficacy of cetuximab as an anti-cancer agent, when used in isolation from 5-FU (see example 1, FIGS. 2 and 3). In addition it was found that the toxic side effects when administering methylene-THF and cetuximab were reduced as compared to when administering methylene-THF and cetuximab in combination with 5-fluorouracil (5-FU) (see example 1, FIG. 4).

These findings led the inventors to provide a novel combination of methylene-THF, THF or methyl-THF and an EGFR inhibitor, in absence or isolation from 5-FU and/or analogues, prodrugs and/or metabolites thereof, for the treatment of cancer. The novel combination of methylene-THF, THF or methyl-THF and an EGFR inhibitor, without 5-FU and/or analogues, prodrugs and/or metabolites thereof, provides a cancer treatment regimen that is more efficient than using an EGFR inhibitor as a single agent, and that has less side effects as compared to a treatment regimen including 5-FU and/or analogues, prodrugs and/or metabolites thereof. Furthermore, such a treatment is useful in cases where 5-FU and/or analogues, prodrugs and/or metabolites thereof cannot be used, e.g. because it is not tolerated by the patient.

As has been described above, folates, such as in the form of leucovorin (folinic acid), tetrahydrofolate (THF) and methylene-THF, are endogenous substances that are essential for cell division and cell growth. For cancer therapy they have been used to alleviate severe side effects of methotrexate and multi-targeting antifolate treatment ((Borsi et al, Pediatric Hematology and Oncology 1990, vol. 7, pages 347-363; EP 1 699 462 B1), and/or to enhance the antitumoral effect of 5-FU and analogous substance such as capecitabine.

Dietary folates are generally available in two supplemental forms, folic acid and leucovorin. Oral administration of folic acid requires a deconjugation step in the small intestine as well as a reduction step into reduced folates in the liver, in order to be available for uptake into cells of the body. Oral administration of leucovorin (also denoted folinic acid or 5-formyltetrahydrofolate) on the other hand, bypasses these deconjugation and reduction steps. Leucovorin seems to be a more metabolically active form of folate than folic acid and, as a reduced folate, might directly cross the blood-brain barrier. Like folic acid, leucovorin must be methylated to become metabolically active. The methylation step of folic acid requires adequate levels of serine and a functional serine hydroxyl-methyl transferase (SHMT) enzyme. Supplementation with the reduced folates methylene-THF and methyl-tetrahydrofolate (methyl-THF) has the advantage of bypassing this methylation step.

Figure 1:
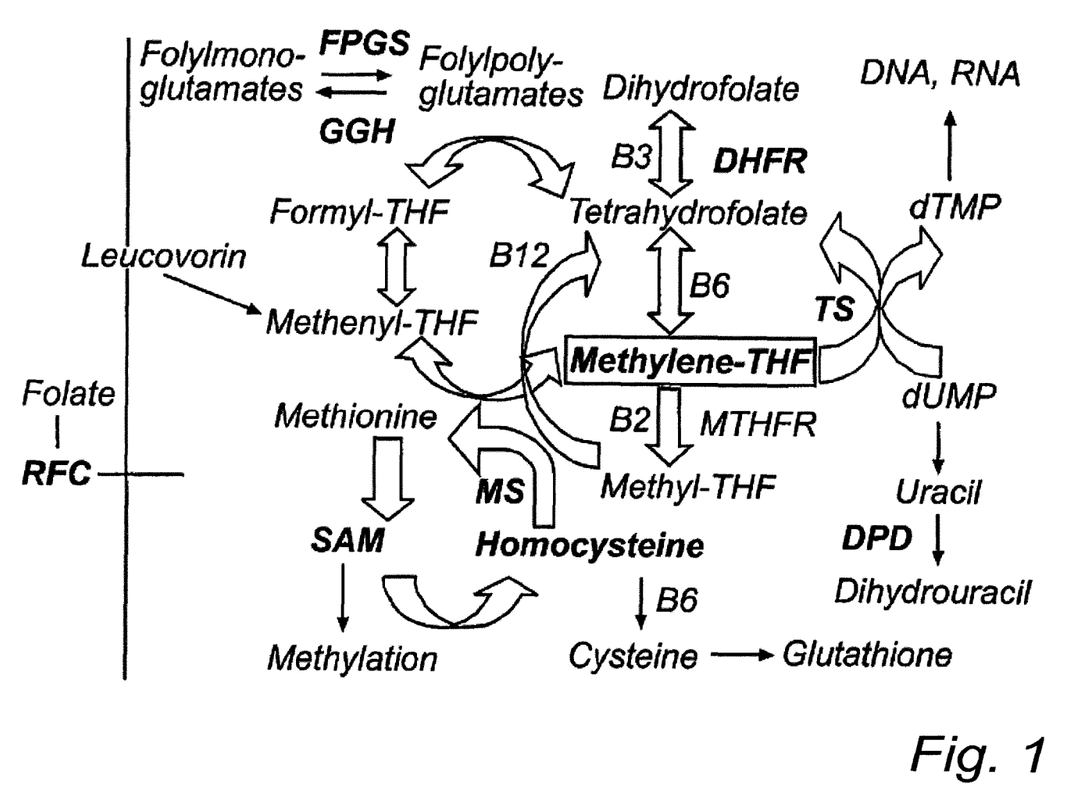
FIG. 1 shows the main metabolic pathways by which folate impact on DNA synthesis, repair and methylation.

FIG. 1 summarizes the main metabolic pathways by which folate and homocysteine have an impact on DNA synthesis, repair and methylation. The enzyme MTHFR balances the DNA methylation and DNA synthesis pathways to maintain normal homeostasis. (RFC=reduced folate carrier; FPGS=folylpolyglutamate synthase; GGH=γ-glutamyl hydrolase; TS=thymidylate synthase; THF=tetrahydrofolate; MTHFR=methylene-tetrahydrofolate reductase; MS=methionine synthase; SAM=S-adenosylmethionine; DPD=dihydro-pyrimidine dehydrogenase; B2=riboflavin; B6=pyridoxine; B12=cobalamin).

The reduced folate carrier, RFC-1, is the major transporter of reduced folates into the cells (Sirotnak F M, Tolner B, "Carrier-mediated membrane transport of folates in mammalian cells"; Annu Rev Nutr 1999; 19:91-122). Intracellularly, reduced folate monoglutamates are converted to polyglutamates by the enzyme folylpolyglutamate synthase (FPGS) (Shane B, "Folylpolyglutamate synthesis and role in the regulation of one-carbon metabolism"; Vitam Horm 1989; 45:263-335). The polyglutamated form of tetrahydrofolate is then further converted to 5,10-methylenetetrahydrofolate (methylene-THF), required as a methyl donor in the conversion of dUMP to dTMP (Spears C P et al, "Deoxyuridylate effects on thymidylate synthase-5-fluorodeoxyuridylate-folate ternary complex formation"; Biochem Pharmacol 1989; 38:2985-93; Spears C P, et al "Thymidylate synthetase inhibition in malignant tumors and normal liver of patients given intravenous 5-fluorouracil", Cancer Res 1984; 44:4144-50). The conversion is catalysed by thymidylate synthase (TS). Methylene-THF is also the precursor of the metabolically active 5-methyltetrahydrofolate (methyl-THF), utilized in the re-methylation of homocysteine. Conversion of methylene-THF to methyl-THF is dependent on the enzyme methylenetetrahydrofolate reductase (MTHFR).

The enzyme γ-glutamyl hydrolase (GGH) catalyzes the degradation of inter- and intracellular polyglutamates (Galivan J et al, "Glutamyl hydrolase. Pharmacological role and enzymatic characterization", Pharmacol Ther 2000; 85:207-15).

As shown, proper functioning of the DNA synthesis and methylation pathways requires riboflavin (vitamin B2), pyridoxine (vitamin B6), and cobalamin (vitamin B12), in addition to folates. Inadequate levels of any of these metabolites will result in elevated homocysteine levels. Pyridoxine deficiency will also impair the cellular ability to produce glutathione, the master antioxidant needed for detoxification of free radicals and alkylating agent damage.

As is shown in FIG. 1, methylene-THF is a normal intracellular metabolite of folic acid, for use in thymidylate synthesis by thymidylate synthase (TS). The same is true with respect to the polyglutamates of methylene-THF. Methylene-THF is also used by several other enzymes including methylene-tetrahydrofolate reductase, serine hydroxymethylase and CI-tetrahydrofolate synthase and methylene-tetrahydrofolate dehydrogenase. These interconversions using methylene-THF are essential for purine synthesis, amino acid synthesis, and lipid metabolism. Thus, methylene-THF is located at a metabolic branch point as a substrate for at least four different enzymes (Spears et al; U.S. Pat. No. 5,376,658).

Thus, methylene-THF has since long been known to propagate cell growth by acting as a one-carbon donor in the conversion between dUMP and dUTP, performed by the enzyme Thymidylate Synthase (TS), and has thus been expected to have a cancer promoting effect.

As stated above, previous studies have shown that folate status may modulate the toxicity and efficacy of cancer chemotherapy. Thus, folic acid and leucovorin, have been used in combination with anti-cancer drugs, e.g. methotrexate in order to mitigate its cytotoxic effects, and 5-FU to increase its anti-cancer effect.

Folic acid, leucovorin and their metabolite methylene-THF are thus known to enhance the chemotherapeutic effect of 5-FU. The enhanced anti-cancer efficacy is achieved by methylene-THF, which strengthens the inhibitory effect of 5-FU on thymidylate synthase (TS). Methylene-THF elicits this increased inhibition by forming a ternary complex with TS and FdUMP, which is a metabolite of 5-FU, thereby strengthening the binding of FdUMP to TS. Thus, in the absence of methylene-THF FdUMP binds to TS extremely weakly. However, in the presence of a large excess of methylene-THF even low levels of FdUMP binds to TS. In the presence of excess methyl-THF the ternary complexes between TS, methyl-THF and FdUMP is stable and no significant TS activity occurs. This efficient inhibition of TS leads to a thymidine-less state of the cell, increased uracil misincorporation into DNA and increased uracil misincorporation into DNA and inhibition of tumor cell growth and cell death. Since methylene-THF is the active substance of folic or leucovorin metabolism, the use of this endogen folate is much more favorable than the use of folic or leucovorin.

For the present disclosure, substances that are analogous to 5-FU are substances that are metabolized to FdUMP. Examples include capecitabine (Xeloda®), floxuridine (5-fluorodeoxyuridine, FUDR), tegafur (Teysuno™, Ftorafur®, UFT) and 5'-deoxyfluorouridine (Doxifluridine™).

Thus, methylene-THF has previously been shown to have anti-cancer effect in combination with 5-FU by strengthening the binding of FdUMP to TS. When administering methylene-THF without co-administration of 5-FU and/or analogues, prodrugs and/or metabolites thereof this mechanism would not occur and thus it would be expected that methylene-THF would not contribute to any anti-cancer effect. The findings of the inventors, that methylene-THF, when used only together with the EGFR inhibitor cetuximab and not with 5-FU, contributes to increased tumor inhibitory activity is therefore very surprising (see example 1).

Thus, for the present disclosure, methylene-THF, or prodrugs or metabolites of methylene-THF, in combination with an EGFR inhibitor such as cetuximab are provided for the treatment of cancer. In one embodiment the combination of an EGFR inhibitor and methylene-THF or prodrugs or metabolites of methylene-THF is provided is isolation of 5-FU and/or analogues, prodrugs and/or metabolites thereof, for the treatment of cancer.

For the present disclosure the EGFR inhibitor may be a small molecule EGFR inhibitor or a monoclonal antibody EGFR inhibitor. Examples of small molecule EGFR inhibitors include gefitinib, erlotinib, and lapatinib. Examples of monoclonal antibody EGFR inhibitors include cetuximab, panitumumab, zalutumumab, nimotuzumab, and matuzumab. EGFR inhibitors that are currently under development are listed in Table 1. Preferably the EGFR inhibitor is cetuximab or panitumumab.

For the present disclosure, methylene-THF, tetrahydrofolate (THF) or methyl-tetrahydrofolate (methyl-THF) may be used in combination with an EGFR inhibitor for the treatment of cancer. Methylene-THF is a folate metabolite that is generally known to exist in equilibrium with THF (see e.g. FIG. 1). Methylene-THF is converted to methyl-THF by the enzyme methylenetetrahydrofolate reductase (MTHFR). Furthermore, methyl-THF is a precursor to THF and methylene-THF.

TABLE 1

| Product | Company | Active Ingredient | Type of substance | Indication |
|---|---|---|---|---|
| BIBW2948BS | Boehringer Ingelheim GmbH (Private) | — | — | Bronchitis (Chronic Obstructive Bronchitis) |
| CGP59326A | Novartis AG (NVS) | — | — | Solid Tumors |
| CP545130 | Pfizer Inc (PFE) | — | — | Human Papilloma Virus Infections |
| EDP13 | BioLineRx, Ltd. (BLRX (TASE)) | — | — | Cancer (Cancers of Epithelial Origin) |
| HMPL309 | Hutchison MediPharma Ltd (Private) | — | — | Cancer |
| JNJ26483327 | Johnson & Johnson (JNJ) | — | — | Solid Tumors (Solid Tumors Unspecified) |
| Novel Tyrosine kinase Inhibitor | Mebiopharm Co Ltd (Private) | — | — | Cancer |
| Tovok with Cetuximab | Boehringer Ingelheim GmbH (Private) | afatinib; cetuximab; sirolimus | Small molecule + mAb | Non-Small-Cell Lung Cancer |
| AG1478 | Algen Biopharmaceuticals Inc. (Private) | — | Small molecule | Psoriasis |
| AL6802 | Advenchen Laboratories, LLC (Private) Simcere Pharmaceutical Group. (SCR) | — | Small molecule | Cancer |
| CO1686 | Avila Therapeutics Inc (Private) Clovis Oncology Inc (CLVS) | — | Small molecule | Non-Small-Cell Lung Cancer |
| MDX214 | Bristol-Myers Squibb Company (BMY) | — | Small molecule | Cancer (EGFr-Expressing Cancer) |
| MT062 | Medisyn Technologies, Inc. (Private) | — | Small molecule | Melanoma (Malignant Melanoma) |
| 111In-NLS-nimotuzumab | YM BioSciences Inc. (YM (TSX)) | nimotuzumab | mAb | Breast Cancer |
| ABT806 | Abbott Laboratories (ABT) | — | mAb | Cancer |
| AFM21 | Affimed Therapeutics AG (Private) | — | mAb | Solid Tumors |
| BIOMAb EGFR | Biocon Ltd (Stock Code Number: 532523 (BSE)) Ferozsons Laboratories Limited (FEROZ (KASE)) | nimotuzumab | mAb | Head and Neck Cancer (Advanced Squamous Cell Head and Neck Cancer) |
| CetuGEX | GLYCOTOPE GmbH (Private) | — | mAb | Solid Tumors (Advanced Solid Tumors) |
| CIMAher | YM BioSciences Inc. (YM (TSX)) Eurofarma (Private) | nimotuzumab | mAb | Brain Tumor (Malignant Astrocytoma in Pediatrics) |

TABLE 1-continued

| Product | Company | Active Ingredient | Type of substance | Indication |
|---|---|---|---|---|
| DXL1218 | InNexus Biotechnology Inc. (IXS (TSXV)) | epidermal growth factor receptor monoclonal antibody | mAb | Colorectal Cancer (Metastatic Colorectal Cancer) |
| EGFR BiTE antibody | Micromet Inc (MITI) | epidermal growth factor receptor antibody (recombinant) | mAb | Solid Tumors (Adenocarcinoma) |
| EGFR Monoclonal Antibody GTC | GTC Biotherapeutics (Private) | epidermal growth factor receptor monoclonal antibody | mAb | Cancer |
| EMD72000 | EMD Serono, Inc. (Private) | matuzumab | mAb | Ovarian Cancer (Recurrent Ovarian Cancer) |
| Erbitux | Bristol-Myers Squibb Company (BMY) Eli Lilly & Co (LLY) ImClone Systems (Private) Merck Serono SA (Private) | cetuximab | mAb | Endometrial Cancer (Progressive or Recurrent Endometrial Cancer) |
| hu806 | Ludwig Institute for Cancer Research Ltd (Private) | — | mAb | Cancer |
| HuMax-EGFr | Genmab A/S (GEN (CPSE)) | Zalutumumab | mAb | Head and Neck Cancer (Advanced Squamous Cell Carcinoma of Head and Neck) |
| IMC11F8 | Eli Lilly & Co (LLY) ImClone Systems (Private) | Necitumumab | mAb | Solid Tumors (Advanced Solid Tumors) |
| MDP01 | Med Discovery SA (Private) | — | mAb | Cancer |
| Monoclonal Antibody 806 LIFE SCIENCE | Life Science Pharmaceuticals (LSP) (Private) | — | mAb | Cancer |
| Nimotuzumab | BioTech Pharmaceuticals Co., Ltd. (Private) | cisplatin; docetaxel; irinotecan; nimotuzumab | mAb | Brain Tumor (Paediatric Brain Tumours) |
| RadioTheraCIM | YM BioSciences Inc. (YM (TSX)) | — | mAb | Brain Tumor |
| RG7160 | F. Hoffmann-La Roche Ltd (ROG (SWX)) | epidermal growth factor receptor monoclonal antibody | mAb | Head and Neck Cancer |
| RG7597 | F. Hoffmann-La Roche Ltd (ROG (SWX)) | epidermal growth factor receptor monoclonal antibody | mAb | Solid Tumors (Metastatic Epithelial Tumors) |
| Sym004 | Symphogen A/S (Private) | epidermal growth factor receptor antibody (recombinant) | mAb | Solid Tumors (Advanced Solid Tumors) |
| TheraCIM | Innogene Kalbiotech (Private) | Nimotuzumab | mAb | Cervical Cancer |
| Vectibix | Amgen Inc (AMGN) | Panitumumab | mAb | Solid Tumors (Solid Tumors in Pediatrics) |
| YMB1005 | YM BioSciences Inc. (YM (TSX)) | epidermal growth factor receptor monoclonal antibody | mAb | Cancer |

Alternative expressions for methylene-THF are e.g. 5,10-methylene tetrahydrofolate, 5,10-methylene-THF, $CH_2FH_4$ and $5,10\text{-}CH_2\text{---}FH_4$. Methylene-THF may e.g. be used in the form of its Ca or $Na_2$ salt, or in the form of various sulfate salts. Further, according to the present disclosure, the free acid may be used, i.e. 5,10-methylene-tetrahydrofolic acid, or 5,10-methylenetetrahydropteroylglutamic acid (5,10-CHz-$H_4$-PteGlu).

Alternative expressions for methyl-THF are e.g. 5-methyl-THF, $CH_3H_4F$ and $5\text{-}CH_3\text{---}H_4F$. Methyl-THF may e.g. be used in the form of its Ca or $Na_2$ salt, or in the form of various sulfate salts. Further, according to the present disclosure, the free acid may be used, i.e. 5-methyl-tetrahydrofolic acid, or methyltetrahydropteroyl-glutamic acid ($5\text{-}CH_3\text{---}H_4PteGlu$).

Alternative expressions for THF are e.g. $H_4F$, $FH_4$ and 5,6,7,8-tetrahydrofolate. THF may e.g. be used in the form of its Ca or $Na_2$ salt, or in the form of various sulfate salts. Further, according to the present disclosure, the free acid may be used, i.e. tetrahydrofolic acid, or tetrahydropteroyl-glutamic acid ($H_4PteGlu$).

THF, methylene-THF and methyl-THF may exist in several isomeric forms, however, the biologically active isomers of THF, methylene-THF and methyl-THF, respectively, are preferred according to the present disclosure. As used herein, "biologically active isomer" relates to an endogen isomer of THF, methylene-THF or methyl-THF, i.e. a natural form which fit into the enzyme systems in the body. One natural, biologically active isomer of THF is [6S]-THF also denoted [6S]-tetrahydrofolic acid. One natural, biologically active isomer of methylene-THF is [6R]-methylene-THF also denoted [6R]-5,10-methylenetetrahydrofolic acid (Modufolin®). And one natural, biologically active isomer of methyl-THF is [6S]-methyl-THF also denoted [6S]-5-methyltetrahydrofolic acid.

Methylene-THF comes in different stereoisomeric forms. The racemic mixture comprises [6R, 6S]-methylene-THF (approximately 50% 6R-configuration and 50% 6S-configuration). However, the [6R]-methylene-THF isoform (approximately 100% 6R-configuration) is the biologically active one. For the present disclosure, [6R]-methylene-THF or [6R, 6S]-methylene-THF may be used. The biologically active isoform, [6R]-methylene-THF, is preferred since it has a more efficient anti-tumoral effect. Natural as well as synthetic methylene-THF or [6R]-methylene-THF may be used. The higher weight portion of a biologically active isomer, the better results will be achieved.

[6R]methylene-THF for use according to the present disclosure suitably has a purity of 90% or higher. A purity of 97% or higher is preferred. The higher weight portion of a biologically active isomer, the better stability will be achieved. At low purities, THF, methylene-THF and methyl-THF are very susceptible to oxidation, and thus unstable.

In one embodiment the combination or composition of an EGFR inhibitor and methylene-THF, THF or methyl-THF, does not comprise 5-FU and/or an analogue, prodrug and/or metabolite thereof. In other words, said combination or composition of an EGFR inhibitor and methylene-THF, THF or methyl-THF, is provided for administration in isolation of or separately from 5-FU and/or an analogue, prodrug and/or metabolite thereof. In one embodiment the combination or composition of an EGFR inhibitor and methylene-THF, THF or methyl-THF, is provided for the treatment of cancer in isolation of, or separately from, other chemotherapeutic agents. In other words, the combination or composition of an EGFR inhibitor and methylene-THF, THF or methyl-THF is in that embodiment not administered simultaneously or concurrently with other anti-cancer drugs.

In one embodiment, the methylene-THF, THF or methyl-THF is administered to the patient no later than three weeks, or two weeks, or 7 days, or 5 days or 3 days or 48 hours or 36 hours or 24 hours before the administration of 5-FU and/or an analogue, prodrug and/or metabolite thereof or, in such embodiments, any other anti-cancer drug. In one embodiment 5-FU and/or analogues, prodrugs and/or metabolites thereof are not administered to the patient before the level in the body of methylene-THF, THF or methyl-THF has sunken below the physiologically active level. The half life of methylene-THF is approximately 20 min, the half life of THF is approximately 30 min and the half life of methyl-THF is approximately 5 hours.

In one embodiment, the methylene-THF, THF or methyl-THF is administered to the patient at the earliest 6 hours, or 12 hours, or 24 hours, or 48 hours, 3 days, or 4 days, or 5 days, or 7 days, or two week or three weeks after the administration of 5-FU and/or an analogue, prodrug and/or metabolite thereof, or any other anti-cancer drug respectively. In one embodiment the methylene-THF, THF or methyl-THF is administered to the patient after the level in the body of the 5-FU and/or an analogue, prodrug and/or metabolite thereof, or, in such embodiments, any other anti-cancer drug, is below a physiologically active level.

By being "provided for administration in isolation of or separately from" is meant that the combination of methylene-THF, THF or methyl-THF and an EGFR inhibitor may be administered no later than one week, two weeks, three weeks, one month, two months or three months before the administration of 5-FU and/or an analogue, prodrug and/or metabolite thereof or, in such embodiments, any other anti-cancer drug respectively. That is, either of the components methylene-THF, THF or methyl-THF or the EGFR inhibitor may be administered no later than one week, two weeks, three weeks, one month, two months or three months before the administration of 5-FU and/or an analogue, prodrug and/or metabolite thereof or any other anti-cancer drug respectively. Alternatively, the combination of methylene-THF, THF or methyl-THF and an EGFR inhibitor may be administered at the earliest one week, two weeks, three weeks, one month, two months or three months after the administration of 5-FU and/or an analogue, prodrug and/or metabolite thereof or any other anti-cancer drug respectively. That is either of the components methylene-THF, THF or methyl-THF or the EGFR inhibitor may be administered no earlier than one week, two weeks, three weeks, one month, two months or three months after the administration of 5-FU and/or an analogue, prodrug and/or metabolite thereof or any other anti-cancer drug.

Methylene-THF, THF or methyl-THF and the EGFR inhibitor may be administered simultaneously or consecutively. In case of consecutive administration either methylene-THF, THF or methyl-THF is administered first and thereafter the EGFR inhibitor, or the EGFR inhibitor is administered first and thereafter methylene-THF, THF or methyl-THF.

The interval between the administrations depends on the drug characteristics and may vary from hours to days. Methylene-THF, THF or methyl-THF may be administered to the patient once or twice daily, every second or third day, once to twice a week, or once every second or third week. The EGFR inhibitor may be administered e.g. every second or third day, once to twice a week, or once every second or third week.

The combination of methylene-THF, THF or methyl-THF and an EGFR inhibitor may be administered to the patient in isolation from 5-FU, and/or analogues, prodrugs and/or metabolites thereof or other anti-cancer drugs during a time period of at least one day or at least one week or two weeks or three weeks or one month or two months or three months or six months or one year or two years. In one embodiment it is administered during a time period of at least three months.

Cetuximab is preferably administered in a dose of 10 mg to 1000 mg, preferably 100-800 mg. The dose for intravenous infusion is at least 50 mg/m² (body surface area), preferably at least 100 mg/m², and more preferably at least 250 mg/m² or approximately 400 mg/m². The maximum dose is approximately 500 mg/m². The dose will be adjusted individually, and may thus vary, e.g. depending on the condition and physiology of the patient. It may, for example, be administered subcutaneously, intramuscularly, intravenously, intra-arterial, intraperitoneally, intranasally or orally.

Methylene-THF, THF or methyl-THF is preferably administered in a dose of 100 pg to 1000 mg, preferably a dose of 100-200 mg. The dose per day ranges between 1 mg and 1000 mg, particularly between 100 mg and 500 mg. The dose is at least 10 mg/m², preferably at least 20 mg/m², more preferably at least 50 mg/m², most preferably at least 100 or 200 mg/m². The maximum dose is approximately 5 g/m² or preferably 1 mg/m² or 500 mg/m². The dose will be adjusted individually, and may thus vary, e.g. depending on the condition and physiology of the patient. It may, for example, be administered subcutaneously, intramuscularly, intravenously, intra-arterial, intraperitoneally, intranasally or orally.

The pharmaceutical composition according to the disclosure may also comprise non-active ingredients, such as an inert vehicle, or pharmaceutical acceptable adjuvants, carriers, preservatives, ascorbic acid, reducing agents, ascorbate, antioxidants, etc, which are well known to persons skilled in the art.

The pharmaceutical composition according to the disclosure may be formulated by conventional manufacturing methods, The methylene-THF, THF or methyl-THF part of the combination may for instance be manufactured by manufacturing methods similar to those used for the production of leucovorin. The methylene-THF of the present disclosure may also be manufactured as described in PCT/EP2004/006944 and patent documents relating thereto.

Examples of cancers to be treated according to the disclosure are breast cancer, gastric cancer, gastrointestinal cancer, gall bladder cancer, bile duct cancer, colon cancer, rectal cancer, liver cancer, pancreatic cancer, head and neck cancer, esophageal cancer, mesothelioma cancer, lung cancer including non-small-cell lung cancer, ovarian cancer, endometrial cancer, cervical cancer, peripheral T-cell lymphoma (PTCL), melanoma, brain tumors, adenocarcinoma, esophageal cancer, and osteosarcoma. However, any cancer may be treated with the pharmaceutical composition according to the present disclosure.

In one embodiment the pharmaceutical composition according to the disclosure is for treatment of cancer, wherein the primary tumor, lymph node metastases and/or distant metastases have a wild type KRAS status, or are wild type in KRAS codons 12 and 13.

In one aspect the present disclosure provides a method for the treatment of cancer comprising administering to a patient a pharmaceutically active amount of an EGFR inhibitor and a pharmaceutically active amount of methylene-THF, THF or methyl-THF.

It should be understood that the embodiments disclosed in relation to the product aspect of the present disclosure are, where applicable, relevant also to the method aspect of the disclosure and vice versa. All characteristics of these compounds that have been described above with respect to the product aspect of the disclosure thus also apply for the method aspect of the disclosure and vice versa.

In one embodiment of the method for treating cancer, said EGFR inhibitor is selected from gefitinib, erlotinib and lapatinib; polyclonal or monoclonal antibody EGFR inhibitors such as cetuximab, panitumumab, zalutumumab, nimotuzumab and matuzumab; and EGFR inhibitors listed in Table 1. Preferably the EGFR inhibitor is a monoclonal antibody. More preferably the monoclonal antibody is cetuximab or panitumumab.

In a preferred embodiment of the method said methylene-THF, THF or methyl-THF is the biologically active isomer of the respective substance. Preferably methylene-THF is administered to the patient and most preferably [6R]-methylene-THF administered.

In one embodiment the method comprises administering the combination or composition of an EGFR inhibitor and methylene-THF, THF or methyl-THF in isolation of or separately from 5-FU and/or an analogue, prodrug and/or metabolite thereof. In another embodiment the combination or composition of an EGFR inhibitor and methylene-THF, THF or methyl-THF, is administered in isolation of, or separately from, other anti-cancer drugs.

By being "provided for administration in isolation of or separately from" is meant that the combination of methylene-THF, THF or methyl-THF and an EGFR inhibitor may be administered no later than one week, two weeks, three weeks, one month, two months or three months before the administration of 5-FU and/or an analogue, prodrug and/or metabolite thereof or, in such embodiments, any other anti-cancer drug respectively. That is, either of the components methylene-THF, THF or methyl-THF or the EGFR inhibitor may be administered no later than one week, two weeks, three weeks, one month, two months or three months before the administration of 5-FU and/or an analogue, prodrug and/or metabolite thereof or any other anti-cancer drug respectively. Alternatively, the combination of methylene-THF, THF or methyl-THF and an EGFR inhibitor may be administered at the earliest one week, two weeks, three weeks, one month, two months or three months after the administration of 5-FU and/or an analogue, prodrug and/or metabolite thereof or any other anti-cancer drug respectively. That is either of the components methylene-THF, THF or methyl-THF or the EGFR inhibitor may be administered no earlier than one week, two weeks, three weeks, one month, two months or three months after the administration of 5-FU and/or an analogue, prodrug and/or metabolite thereof or any other anti-cancer drug.

In one embodiment the method comprises administering methylene-THF, THF or methyl-THF of the combination to the patient no later than three weeks, or two weeks, or 7 days, or 5 days or 3 days or 48 hours or 36 hours or 24 hours before the administration of 5-FU, and/or an analogue, prodrug and/or metabolite thereof or any other anti-cancer drug. In one embodiment 5-FU, and/or analogues, prodrugs and/or metabolites thereof or any other anti-cancer drug are not administered to the patient before the level in the body of methylene-THF, THF or methyl-THF has sunken below a physiologically active level. The method may also or alternatively comprise administering methylene-THF, THF or methyl-THF to the patient at the earliest 6 hours, or 12 hours, or 24 hours, or 48 hours, 3 days, or 4 days, or 5 days, or 7 days, or two week or three weeks after the administration of 5-FU and/or analogues, prodrugs and/or metabolites thereof or any other anti-cancer drug or any other pharmaceutically active agent respectively. In one embodiment the methylene-THF, THF or methyl-THF is administered to the patient after the level in the body of the 5-FU and/or analogue, prodrug and/or metabolite thereof, or, in such embodiments, any other anti-cancer drug, is below a physiologically active level.

The methylene-THF, THF or methyl-THF and EGFR inhibitor may be administered in doses, time intervals and order as specified above for the product aspect of the disclosure. The methylene-THF, THF or methyl-THF and the EGFR inhibitor may for instance be administered consecutively or simultaneously.

The cancer to be treated may be selected from breast cancer, gastric cancer, gastrointestinal cancer, gall bladder cancer, bile duct cancer, colon cancer, rectal cancer, liver cancer, pancreatic cancer, head and neck cancer, esophageal cancer, mesothelioma cancer, lung cancer including non-small-cell lung cancer, ovarian cancer, endometrial cancer, cervical cancer, peripheral T-cell lymphoma (PTCL), melanoma, brain tumors, adenocarcinoma, esophageal cancer, and osteosarcoma. However, any cancer may be treated with the pharmaceutical composition according to the present disclosure The term "chemotherapeutic agent" or "anti-cancer agent" or "anti-cancer drug" as used herein relates to a medicament for the treatment of cancer, i.e. it relates to an agent/active ingredient having an anti-cancer or anti-tumoral effect. Such an effect may involve inhibition of tumor growth, reduction in tumor volume, induction of tumor cell death, inhibition of formation of metastasis, inhibition of tumor recurrence.

The term "patient" as used herein relates to any human or non-human mammal in need of being treated with the methods, kit or pharmaceutical compositions according to the disclosure.

The term "treatment" as used herein relates to both treatment in order to cure or alleviate the symptoms of different types of cancer, and to treatment in order to prevent the development of cancer or prevent the recurrence of cancer. In particular, solid tumors are well suited to be treated according to the disclosure. However, both solid and non-solid tumors may be treated.

The term "pharmaceutically active amount" as used herein relates to a dose of a substance that will lead to the desired pharmacological and/or therapeutic effect. The desired pharmacological and/or therapeutic effect is, as stated above, to cure or alleviate the symptoms of different types of cancer, and to prevent the development of cancer.

The term "physiologically active level" as used herein relates to a level of a substance within the body of a patient, e.g. the circulating level in blood, at which the desired physiological effect is achieved. Below this level the physiological effect is not achieved or is not detectable. The physiological effect of an anti-cancer drug may for instance be inhibition of tumor growth, reduction in tumor volume, induction of tumor cell death, inhibition of formation of metastasis, inhibition of tumor recurrence.

The term "efficacy" of a chemotherapeutic or anti-cancer treatment relates to its ability to affect tumor and cancer cells and to improve the clinical results of the treatment. Such efficacy can be determined e.g. by measuring remission, time to progression, response rate and survival. Methods for measuring such parameters are well-established in the field. For example, anti-tumor effects can be determined by measuring tumor size and tumor size over time.

EXAMPLE

Purpose: To determine the anti-tumoral efficacy of methylene-THF in combination with cetuximab in the colorectal adenocarcinoma xenograft model LoVo. LoVo is a cell line that is sensitive to cetuximab and 5-FU.

Study Design: A total of 50 female NCr nu/nu mice (10 per group) at the age of 8-12 weeks were injected with $1 \times 10^7$ LoVo tumor cells in 50% Matrigel sc in flank. After seven days they were administered intraperitoneal injections according to the schedule in table 2. Animals were monitored individually. The endpoint of the experiment was a tumor weight of 1000 mm$^3$ or 75 days, whichever came first. Responders could be followed longer. When the endpoint was reached, the animals were euthanized. Body weight (g) and tumor volume (mm$^3$) was measured on days 1, 2, 3, 4, 5, 7, 11, 14, 18, 21, 25, 28, 32, 35, 39, 42, 46, 49, 53, 56, 60, 63, 67, 70 and 74.

TABLE 2

Treatment groups and dosing

| Group | Vehicle | Cetuximab (100 mg/kg, biwk × 4) | 5-FU (100 mg/kg, qwk × 3) | Methylene-THF (45 mg/kg, 3/4/3/4/3) |
|---|---|---|---|---|
| 1 | X | | | |
| 2 | | X | | |
| 3 | | X | | X |
| 4 | | X | X | |
| 5 | | X | X | X | biwk = every other week
qwk = weekly
3/4/3/4/3 = treatment for three days, no treatment for four days Results A summary of the data achieved is shown in table 3.

TABLE 3

Overview.

| Group | No of TP | No of treatment related deaths | No of non-treatment related deaths | Median Time to Endpoint (days) | Percent tumor growth delay (TGD) |
|---|---|---|---|---|---|
| 1 | 10 | 0 | 0 | 25.5 | — |
| 2 | 8 | 0 | 1 | 56.7 | 122 |
| 3 | 8 | 0 | 0 | 61 | 139 |
| 4 | 5 | 0 | 0 | 69.4 | 172 |
| 5 | 5 | 0 | 0 | 72 | 182 |

Tumor Volume

The change in median tumor volume over time is shown in FIG. 2. The animals in the vehicle group, i.e. group 1, reached the endpoint early. The figure indicates that methylene-THF has a beneficial effect on tumor growth and enhances the anti-tumor effect of cetuximab. Surprisingly, the beneficial effect of methylene-THF is seen even in the absence of 5-FU.

Survival Time

A Kaplan-Meier plot showing the time to end point, i.e. when a tumor weight of 1000 mm$^3$ or 75 days was reached, in the respective groups is displayed in FIG. 3. The Kaplan-Meier curve (time to endpoint) shows a beneficial effect of methylene-THF, methylene-THF enhancing the beneficial effect of cetuximab. A log-rank test shows that there is a statistically significant difference between the treatment groups also when the vehicle group is excluded.

Body Weight

Figure 4:
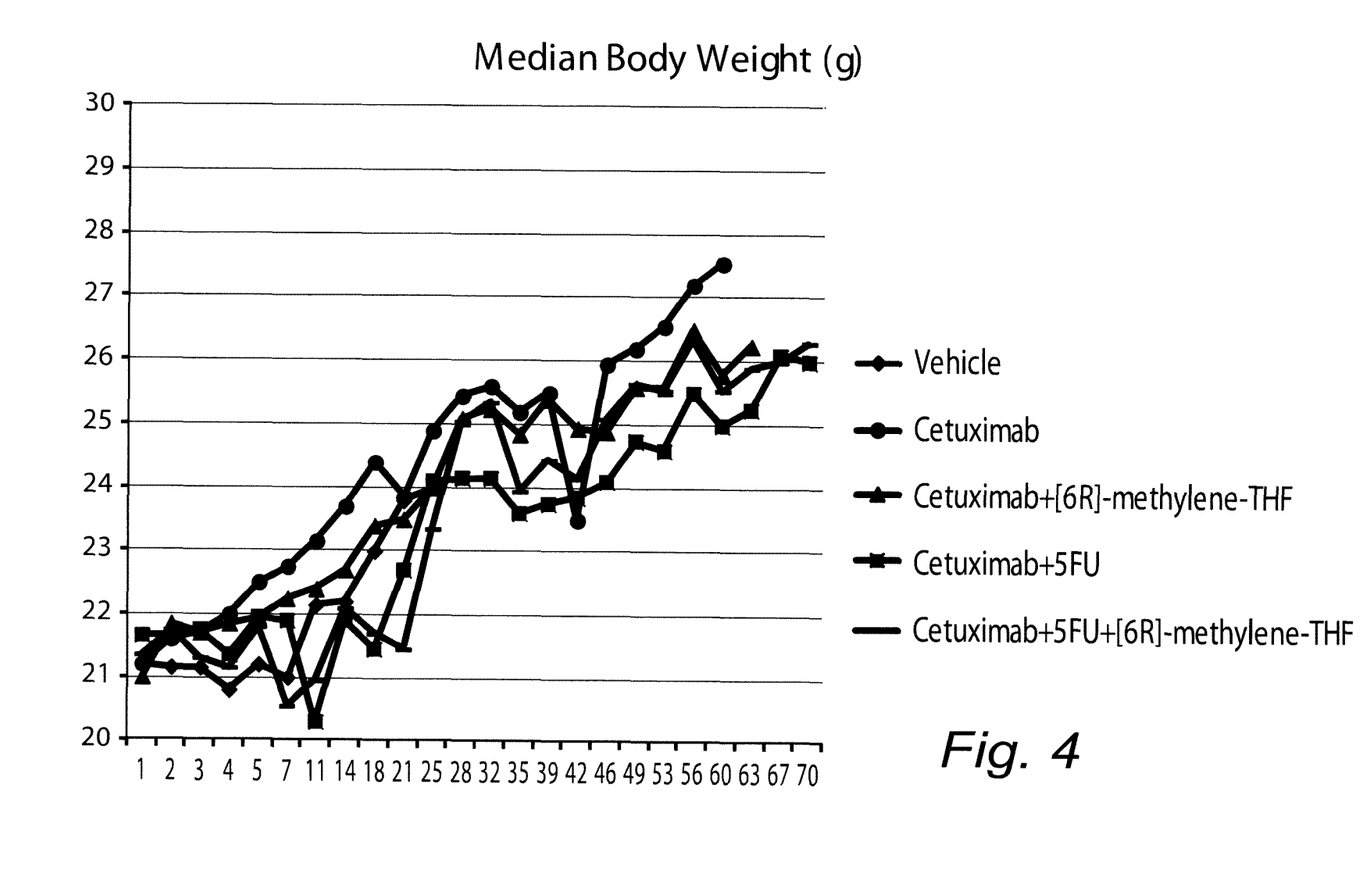
FIG. 4 shows the development of median body weight over time in the respective animal groups of example 1.

Body weight gives an indication on how severe the side effects of the treatment are, poor development of body weight indicating more adverse side effects. Both treatment groups with methylene-THF, i.e. groups 3 and 5, show quite similar development of body weight as seen in FIG. 4. The group with the poorest development of body weight from day 28 and on was group 4 that received cetuximab and 5-FU.

CONCLUSION

It appears that the group that received cetuximab in combination with 5-FU and methylene-THF had the most favorable development considering both tumor volume, i.e. tumor growth inhibition, and body weight, i.e. less severe side effects. The group that received only cetuximab had the least favorable development considering tumor volume but had a weight increase better than the other groups including vehicle. Surprisingly, methylene-THF enhances the anti-tumor growth effect of cetuximab, even in the absence of 5-FU.

The invention claimed is:

1. A method for the treatment of an EGFR-expressing cancer in a patient in need thereof, the method comprising administering to a patient a pharmaceutically active amount of a pharmaceutical composition comprising:
   a) methylene-tetrahydrofolate, and
   b) cetuximab;
   wherein said composition is administered in isolation of 5-fluorouracil and in isolation of analogues, prodrugs and/or metabolites of 5-fluorouracil.

2. The method according to claim 1, wherein component a) is administered no later than 24 hours before the administration of 5-FU and/or an analogue, prodrug and/or metabolite thereof.

3. The method according to claim 1, wherein component a) is administered no later than 36 hours before the administration of 5-FU and/or an analogue, prodrug and/or metabolite thereof.

4. The method according to claim 1, wherein component a) is administered no later than 48 hours before the administration of 5-FU and/or an analogue, prodrug and/or metabolite thereof.

5. The method according to claim 1, wherein component a) is administered at the earliest 6 hours after the administration of 5-FU and/or an analogue, prodrug and/or metabolite thereof.

6. The method according to claim 1, wherein component a) is administered at the earliest 24 hours after the administration of 5-FU and/or an analogue, prodrug and/or metabolite thereof.

7. The method according to claim 1, wherein component a) is administered at the earliest 48 hours after the administration of 5-FU and/or an analogue, prodrug and/or metabolite thereof.

8. The method according to claim 1, wherein component a) is administered at the earliest one week after the administration of 5-FU and/or an analogue, prodrug and/or metabolite thereof.

9. The method according to claim 1, wherein component a) is administered at the earliest 12 days after the administration of 5-FU and/or an analogue, prodrug and/or metabolite thereof.

10. The method according to claim 1, wherein said composition is administered no later than one week before the administration of 5-FU and/or an analogue, prodrug and/or metabolite thereof.

11. The method according to claim 1, wherein said composition is administered at the earliest one week after the administration of 5-FU and/or an analogue, prodrug and/or metabolite thereof.

12. The method according to claim 1, wherein said composition is administered in isolation from 5-FU and/or an analogue, prodrug and/or metabolite thereof during a time period of at least 3 months.

13. The method according to claim 1, wherein component a) and component b) are formulated in different pharmaceutical compositions.

14. The method according to claim 1, wherein component a) and component b) are formulated in a common pharmaceutical composition.

15. The method according to claim 1, wherein component b) is administered in an amount of at least 50 mg/m$^2$ and at maximum 1000 mg/m$^2$.

16. The method according to claim 1, wherein component a) is administered in an amount of at least 10 mg/m$^2$ and at maximum 5 g/m$^2$.

17. The method according to claim 1, wherein said cancer is selected from breast cancer, gastric cancer, gastrointestinal cancer, gall bladder cancer, bile duct cancer, colon cancer, rectal cancer, liver cancer, pancreatic cancer, head and neck cancer, esophageal cancer, mesothelioma cancer, lung cancer including non-small-cell lung cancer, ovarian cancer, endometrial cancer, cervical cancer, peripheral T-cell lymphoma (PTCL), melanoma, brain tumors, adenocarcinoma, esophageal cancer, and osteosarcoma.

18. A method for inhibiting tumor growth of an EGFR-expressing tumor in a patient in need thereof, the method comprising administering to a patient a pharmaceutically active amount of a pharmaceutical composition comprising methylene-tetrahydrofolate and cetuximab; wherein said composition is administered in isolation of 5-fluorouracil and in isolation of analogues, prodrugs and/or metabolites of 5-fluorouracil.

19. A method for reducing tumor volume of an EGFR-expressing tumor in a patient in need thereof, the method comprising administering to a patient a pharmaceutically active amount of a pharmaceutical composition comprising methylene-tetrahydrofolate and cetuximab; wherein said composition is administered in isolation of 5-fluorouracil and in isolation of analogues, prodrugs and/or metabolites of 5-fluorouracil.

* * * * *